United States Patent
Knowlton

(10) Patent No.: US 11,090,473 B2
(45) Date of Patent: *Aug. 17, 2021

(54) SKIN TREATMENT DEVICE

(71) Applicant: SRGI HOLDINGS, LLC, Henderson, NV (US)

(72) Inventor: Edward W. Knowlton, Henderson, NV (US)

(73) Assignee: SRGI HOLDINGS, LLC, Henderson, NV (US)

( * ) Notice: Subject to any disclaimer, the term of this patent is extended or adjusted under 35 U.S.C. 154(b) by 170 days.

This patent is subject to a terminal disclaimer.

(21) Appl. No.: 15/997,316

(22) Filed: Jun. 4, 2018

(65) Prior Publication Data

US 2019/0134365 A1 May 9, 2019

Related U.S. Application Data

(63) Continuation of application No. 14/556,648, filed on Dec. 1, 2014, now Pat. No. 9,987,473, which is a
(Continued)

(51) Int. Cl.
*A61M 35/00* (2006.01)
*A61B 17/3205* (2006.01)
(Continued)

(52) U.S. Cl.
CPC ......... *A61M 35/003* (2013.01); *A61B 17/322* (2013.01); *A61B 17/32053* (2013.01);
(Continued)

(58) Field of Classification Search
CPC ........... A61M 35/003; A61B 17/32053; A61B 17/32093; A61B 17/322;
(Continued)

(56) References Cited

U.S. PATENT DOCUMENTS

| 1,610,089 A | * | 12/1926 | Heitler | A61F 15/006 |
| | | | | 602/42 |
| 3,613,242 A | | 10/1971 | Hill et al. | |

(Continued)

FOREIGN PATENT DOCUMENTS

| CN | 101530636 B | 2/2012 |
| KR | 200303833 Y1 | 8/2003 |

(Continued)

OTHER PUBLICATIONS

Ablaza V.J., et al., "An Alternative Treatment for the Split Skin-Graft Donor Site," Aesthetic Plastic Surgery, 1997, vol. 21 (3), pp. 207-209.

(Continued)

*Primary Examiner* — Bradley J Osinski
(74) *Attorney, Agent, or Firm* — IPR Law Group PC

(57) ABSTRACT

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

21 Claims, 10 Drawing Sheets

Related U.S. Application Data continuation of application No. 12/972,013, filed on Dec. 17, 2010, now Pat. No. 8,900,181.

(60) Provisional application No. 61/288,141, filed on Dec. 18, 2009.

(51) Int. Cl.

| | |
|---|---|
| *A61B 17/3209* | (2006.01) |
| *A61B 17/322* | (2006.01) |
| *A61M 5/46* | (2006.01) |
| *A61B 17/32* | (2006.01) |
| *A61B 17/00* | (2006.01) |

(52) U.S. Cl.
CPC ......... *A61B 17/32093* (2013.01); *A61M 5/46* (2013.01); *A61B 2017/00424* (2013.01); *A61B 2017/00747* (2013.01); *A61B 2017/00761* (2013.01); *A61B 2017/00792* (2013.01); *A61B 2017/3225* (2013.01); *A61B 2017/320064* (2013.01)

(58) Field of Classification Search
CPC ...... A61B 2017/0398; A61B 2217/005; A61B 2017/00769; A61B 2017/320064; A61B 2017/00761
See application file for complete search history.

(56) References Cited

U.S. PATENT DOCUMENTS

| | | | |
|---|---|---|---|
| 3,820,543 A | 6/1974 | Vanjushin et al. | |
| 3,867,942 A | 2/1975 | Bellantoni et al. | |
| 4,018,228 A | 4/1977 | Goosen | |
| 4,098,278 A | 7/1978 | Schwartz | |
| 4,160,453 A | 7/1979 | Miller | |
| 4,476,864 A | 10/1984 | Tezel | |
| 4,542,742 A | 9/1985 | Winkelman et al. | |
| 4,582,640 A | 4/1986 | Smestad et al. | |
| 4,803,075 A | 2/1989 | Wallace et al. | |
| 4,944,737 A | 7/1990 | Bloom | |
| 5,123,907 A | 6/1992 | Romaine | |
| 5,141,513 A | 8/1992 | Fortune et al. | |
| 5,209,755 A | 5/1993 | Abrahan et al. | |
| 5,415,182 A | 5/1995 | Chin et al. | |
| 5,417,683 A | 5/1995 | Shiao | |
| 5,570,700 A | 11/1996 | Vogeler | |
| 5,578,054 A | 11/1996 | Arnold | |
| 5,591,444 A | 1/1997 | Boss, Jr. | |
| 5,643,308 A | 7/1997 | Markman | |
| 5,665,372 A | 9/1997 | Boss, Jr. | |
| 5,693,064 A | 12/1997 | Arnold | |
| 5,827,297 A | 10/1998 | Boudjema | |
| 5,858,019 A | 1/1999 | Ashraf | |
| 5,871,495 A | 2/1999 | Mueller | |
| 5,879,326 A | 3/1999 | Godshall et al. | |
| 5,895,403 A | 4/1999 | Collinsworth | |
| 5,922,000 A | 7/1999 | Chodorow | |
| 5,928,162 A | 7/1999 | Giurtino et al. | |
| 5,964,729 A | 10/1999 | Choi et al. | |
| 5,970,709 A | 10/1999 | Tohji | |
| 5,989,278 A | 11/1999 | Mueller | |
| 6,027,512 A | 2/2000 | Bridges | |
| 6,059,807 A | 5/2000 | Boudjema | |
| 6,126,615 A | 10/2000 | Allen et al. | |
| 6,432,710 B1 | 8/2002 | Boss, Jr. et al. | |
| 6,471,712 B2 * | 10/2002 | Burres ................... | A45D 29/14 606/131 |
| 6,497,875 B1 | 12/2002 | Sorrell et al. | |
| 6,572,625 B1 | 6/2003 | Rassman | |
| 6,585,746 B2 | 7/2003 | Gildenberg | |
| 6,589,202 B1 | 7/2003 | Powell | |
| 6,626,865 B1 | 9/2003 | Prisell | |
| 6,669,685 B1 | 12/2003 | Rizoiu et al. | |
| 6,997,923 B2 | 2/2006 | Anderson et al. | |
| 7,204,828 B2 | 4/2007 | Rosiello | |
| 7,261,721 B2 | 8/2007 | Feller | |
| 7,316,822 B2 | 1/2008 | Binette et al. | |
| 7,331,953 B2 | 2/2008 | Manstein et al. | |
| 7,354,423 B2 | 4/2008 | Zelickson et al. | |
| 7,412,978 B1 | 8/2008 | Keller | |
| 7,621,933 B2 | 11/2009 | Bodduluri et al. | |
| 7,625,384 B2 * | 12/2009 | Eriksson ............... | A61B 17/322 606/132 |
| 7,708,746 B2 | 5/2010 | Eriksson et al. | |
| 7,846,465 B1 | 12/2010 | Keller et al. | |
| 7,942,153 B2 | 5/2011 | Manstein et al. | |
| 7,962,192 B2 | 6/2011 | Bodduluri et al. | |
| 7,993,310 B2 | 8/2011 | Rosiello | |
| 8,062,322 B2 | 11/2011 | Rassman et al. | |
| 8,202,279 B2 | 6/2012 | Cole | |
| 8,211,134 B2 | 7/2012 | Oostman, Jr. | |
| 8,317,804 B1 | 11/2012 | Rassman et al. | |
| 8,486,155 B2 | 7/2013 | McAlister et al. | |
| 8,529,883 B2 | 9/2013 | Maslowski | |
| 8,535,299 B2 | 9/2013 | Giovannoli | |
| 8,540,731 B2 * | 9/2013 | Kay ....................... | A61B 17/54 606/131 |
| 8,545,489 B2 | 10/2013 | Giovannoli | |
| 8,690,863 B2 | 4/2014 | Chan et al. | |
| 8,728,819 B2 | 5/2014 | Maslowski et al. | |
| 8,765,121 B2 | 7/2014 | Maslowski | |
| 8,900,181 B2 | 12/2014 | Knowlton | |
| 8,986,324 B2 | 3/2015 | Bodduluri et al. | |
| 9,005,218 B2 | 4/2015 | Harris | |
| 9,060,803 B2 | 6/2015 | Anderson et al. | |
| 9,095,368 B2 | 8/2015 | Umar et al. | |
| 9,351,792 B2 | 5/2016 | Manstein et al. | |
| 9,415,075 B2 | 8/2016 | Maslowski | |
| 9,439,673 B2 | 9/2016 | Austen | |
| 9,468,459 B2 | 10/2016 | Hall et al. | |
| 9,743,949 B2 | 8/2017 | Guiles et al. | |
| D797,286 S | 9/2017 | Ginggen et al. | |
| 9,902,937 B2 | 2/2018 | Maslowski et al. | |
| 10,098,914 B2 | 10/2018 | Maslowski | |
| 10,117,721 B2 | 11/2018 | Tripathi et al. | |
| 10,219,827 B2 | 3/2019 | Knowlton et al. | |
| 10,251,792 B2 | 4/2019 | Levinson et al. | |
| 10,335,190 B2 | 7/2019 | Knowlton | |
| 10,368,904 B2 | 8/2019 | Knowlton | |
| 2001/0053888 A1 | 12/2001 | Athanasiou et al. | |
| 2002/0052619 A1 | 5/2002 | Transue | |
| 2002/0088779 A1 | 7/2002 | Neev et al. | |
| 2002/0111563 A1 | 8/2002 | Hall | |
| 2002/0183688 A1 | 12/2002 | Lastovich et al. | |
| 2003/0036770 A1 | 2/2003 | Markman | |
| 2003/0069548 A1 | 4/2003 | Connelly et al. | |
| 2003/0216719 A1 | 11/2003 | Debenedictis et al. | |
| 2004/0082940 A1 | 4/2004 | Black et al. | |
| 2004/0087893 A1 | 5/2004 | Kwon | |
| 2004/0087992 A1 | 5/2004 | Gartstein et al. | |
| 2004/0175690 A1 | 9/2004 | Mishra et al. | |
| 2004/0210214 A1 | 10/2004 | Knowlton | |
| 2005/0049582 A1 | 3/2005 | Debenedictis et al. | |
| 2005/0154331 A1 | 7/2005 | Christie et al. | |
| 2005/0154431 A1 | 7/2005 | Quistgaard et al. | |
| 2005/0171504 A1 | 8/2005 | Miller | |
| 2005/0267506 A1 | 12/2005 | Harris | |
| 2005/0283141 A1 | 12/2005 | Giovannoli | |
| 2006/0051404 A1 | 3/2006 | Yeshurun et al. | |
| 2006/0155266 A1 | 7/2006 | Manstein et al. | |
| 2007/0038236 A1 | 2/2007 | Cohen | |
| 2007/0073217 A1 | 3/2007 | James | |
| 2007/0073327 A1 | 3/2007 | Giovannoli | |
| 2007/0179481 A1 | 8/2007 | Frangineas et al. | |
| 2007/0179516 A1 | 8/2007 | Mishra et al. | |
| 2007/0207131 A1 | 9/2007 | Boss, Jr. et al. | |
| 2007/0224173 A1 | 9/2007 | Koullick et al. | |
| 2007/0293884 A9 | 12/2007 | Cole et al. | |
| 2008/0172047 A1 | 7/2008 | Altshuler et al. | |
| 2008/0275378 A1 | 11/2008 | Herndon | |
| 2009/0048558 A1 | 2/2009 | Del Vecchio | |
| 2010/0114118 A1 | 5/2010 | Harris | |

(56) References Cited

U.S. PATENT DOCUMENTS

| | | |
|---|---|---|
| 2010/0121307 A1 | 5/2010 | Lockard et al. |
| 2010/0204722 A1 | 8/2010 | Gilsdorf |
| 2010/0303770 A1 | 12/2010 | Maslowski et al. |
| 2011/0009860 A1 | 1/2011 | Chornenky et al. |
| 2011/0077664 A1 | 3/2011 | Schulz et al. |
| 2011/0177591 A1 | 7/2011 | Iwatschenko et al. |
| 2011/0208089 A1 | 8/2011 | Sundheimer et al. |
| 2011/0251602 A1 | 10/2011 | Anderson et al. |
| 2011/0257588 A1 | 10/2011 | Knowlton |
| 2011/0264115 A1 | 10/2011 | Asrani et al. |
| 2011/0282239 A1 | 11/2011 | Conlon et al. |
| 2011/0282382 A1 | 11/2011 | McAlister et al. |
| 2011/0313429 A1 | 12/2011 | Anderson et al. |
| 2012/0022510 A1 | 1/2012 | Welches et al. |
| 2012/0035599 A1 | 2/2012 | Sabir et al. |
| 2012/0041430 A1 | 2/2012 | Anderson et al. |
| 2012/0219634 A1 | 8/2012 | Maslowski et al. |
| 2012/0226214 A1 | 9/2012 | Gurtner et al. |
| 2012/0271320 A1 | 10/2012 | Hall et al. |
| 2012/0323139 A1 | 12/2012 | Richardson |
| 2012/0323325 A1 | 12/2012 | Fulton |
| 2013/0006168 A1 | 1/2013 | Del Vecchio |
| 2013/0090669 A1 | 4/2013 | Bellomo et al. |
| 2013/0096600 A1 | 4/2013 | Wesley et al. |
| 2013/0204273 A1 | 8/2013 | Sabir et al. |
| 2013/0236427 A1 | 9/2013 | Pernock |
| 2013/0287286 A1 | 10/2013 | Zingaretti et al. |
| 2013/0295061 A1 | 11/2013 | Maslowski |
| 2013/0304090 A1 | 11/2013 | Oostman, Jr. et al. |
| 2013/0345721 A1 | 12/2013 | Menke et al. |
| 2014/0031801 A1 | 1/2014 | Giovannoli |
| 2014/0099383 A1 | 4/2014 | Maslowski et al. |
| 2014/0277055 A1 | 9/2014 | Austen, Jr. |
| 2014/0296741 A1 | 10/2014 | Austen |
| 2014/0303648 A1 | 10/2014 | Knowlton |
| 2014/0343575 A1 | 11/2014 | Andreani et al. |
| 2015/0018844 A1 | 1/2015 | Harris |
| 2015/0173991 A1 | 6/2015 | Anderson et al. |
| 2015/0201955 A1 | 7/2015 | Sabir et al. |
| 2015/0216545 A1 | 8/2015 | Anderson et al. |
| 2015/0230818 A1 | 8/2015 | Knowlton |
| 2015/0238214 A1 | 8/2015 | Anderson et al. |
| 2015/0250493 A1 | 9/2015 | Umar |
| 2015/0366719 A1 | 12/2015 | Levinson et al. |
| 2016/0008515 A1 | 1/2016 | Stilwell et al. |
| 2016/0095592 A1 | 4/2016 | Levinson et al. |
| 2016/0166272 A1 | 6/2016 | Shiao |
| 2016/0192961 A1 | 7/2016 | Ginggen et al. |
| 2016/0287281 A1 | 10/2016 | Knowlton |
| 2016/0310157 A1 | 10/2016 | Guiles et al. |
| 2016/0310158 A1 | 10/2016 | Guiles et al. |
| 2016/0310159 A1 | 10/2016 | Guiles et al. |
| 2016/0310444 A1 | 10/2016 | Dobak, III |
| 2016/0317170 A1 | 11/2016 | Knowlton |
| 2016/0317721 A1 | 11/2016 | Ginggen et al. |
| 2016/0340651 A1 | 11/2016 | Maslowski et al. |
| 2016/0367280 A1 | 12/2016 | Austen |
| 2017/0042561 A1 | 2/2017 | Hall et al. |
| 2017/0079824 A1 | 3/2017 | Thompson |
| 2017/0296214 A1 | 10/2017 | Knowlton |
| 2017/0333068 A1 | 11/2017 | Knowlton |
| 2017/0367729 A1 | 12/2017 | Ginggen et al. |
| 2018/0006300 A1 | 1/2018 | Jeong et al. |
| 2018/0036029 A1 | 2/2018 | Anderson et al. |
| 2018/0078278 A1 | 3/2018 | Levinson et al. |
| 2018/0161056 A1 | 6/2018 | Kim et al. |
| 2018/0325543 A1 | 11/2018 | Skog et al. |
| 2018/0346878 A1 | 12/2018 | Maslowski et al. |
| 2019/0015255 A1 | 1/2019 | Gurtner et al. |
| 2019/0046777 A1 | 2/2019 | Knowlton |
| 2019/0099199 A1 | 4/2019 | Levinson et al. |

FOREIGN PATENT DOCUMENTS

| | | |
|---|---|---|
| KR | 20080100795 A | 11/2008 |
| WO | 014556 A1 | 6/2001 |
| WO | 2005072181 A2 | 8/2005 |
| WO | 2008002064 A1 | 1/2008 |
| WO | 2009146068 A1 | 12/2009 |
| WO | 2012103483 A2 | 8/2012 |
| WO | 2012136904 A1 | 10/2012 |
| WO | 2013013196 A1 | 1/2013 |
| WO | 2013013199 A2 | 1/2013 |
| WO | 2014028626 A1 | 2/2014 |
| WO | 2014089488 A2 | 6/2014 |
| WO | 2015051164 A2 | 4/2015 |

OTHER PUBLICATIONS

Akan M., et al., "An Alternative Method to Minimize Pain in the Split-Thickness Skin Graft Donor Site," Plastic and Reconstructive Surgery, Aug. 2002, vol. 111 (7), pp. 2243-2249.

Alguire P.C et al., "Skin Biopsy Techniques for the Internist," Journal of General Internal Medicine, Jan. 1998, vol. 13 (1), pp. 46-54.

Andreassi A., et al., "Classification and Pathophysiology of Skin Grafts," Clinics in Dermatology, 2005, vol. 23 (4), pp. 332-337.

Bello Y.M., et al., "Tissue-Engineered Skin, Current Status in Wound Healing," American Journal Clinical Dermatology, 2001, vol. 2 (5), pp. 305-313.

Branski L.K., et al., "A Porcine Model of Full-Thickness Burn, Excision, and Skin Autographing," Burns, 2008, vol. 34 (8), pp. 1119-1127.

Burns J.A., "Thermage: Monopolar Radiofrequency," Aesthetic Surgery Journal, Nov./Dec. 2005, vol. 25 (6), pp. 638-642.

Cirodde A., et al., "Cultured Epithelial Autografts in Massive Burns: A Single-Center Retrospective Study with 63 Patients," Burns, 2011, vol. 37 (6), pp. 964-972.

Clugston P.A., et al., "Cultured Epithelial Autografts: Three Years of Clinical Experience with Eighteen Patients," Journal of Burn Care and Rehabilitation, 1991, vol. 12 (6), pp. 533-539.

Cooperman L.S., et al., "Injectable Collagen: A Six-Year Clinical Investigation," Aesthetic Plastic Surgery, Jun. 1985, vol. 9 (2), pp. 145-151.

Dornseifer U., et al., "The Ideal Split-Thickness Skin Graft Donor Site Dressing: Rediscovery of Polyurethane Film," Annals of Plastic Surgery, Aug. 2009, vol. 63 (2), pp. 198-200.

Dornseifer U., et al., "The Ideal Split-Thickness Skin Graft Donor-Site Dressing: A Clinical Comparative Trial of a Modified Polyurethane Dressing and Aquacel," Plastic and Reconstructive Surgery, 2011, vol. 128 (4), pp. 918-924.

Elliot M., et al., "Initial Experience with Cultured Epithelial Autografts in Massively Burnt Patients," ANZ Journal of Surgery, 2002, vol. 72 (11), pp. 893-895.

Extended European Search Report for Application No. EP05027935 dated Jun. 12, 2009, 4 pages.

Fischer J.P., et al., "Complications in Body Contouring Procedures: An Analysis of 1797 Patients from the 2005 to 2010 American College of Surgeons National Surgical Quality Improvement Program Databases," Plastic and Reconstructive Surgery, 2013, vol. 132 (6), pp. 1411-1420.

Ford C.N., et al., "A Preliminary Study of Injectable Collagen in Human Vocal Fold Augmentation," Otolaryngology—Head and Neck Surgery, Jan. 1986, vol. 94 (1), pp. 104-112.

Ford C.N., et al., "Autologous Collagen Vocal Fold Injection: A Preliminary Clinical Study," Laryngoscope, Sep. 1995, vol. 105 (9 Pt 1), pp. 944-998.

Ford C.N., et al., "Clinical Experience with Injectable Collagen for Vocal Fold Augmentation," Larynscope, Aug. 1986, vol. 96 (8), pp. 863-869.

Ford C.N., et al., "Role of Injectable Collagen in the Treatment of Glottic Insufficiency: A Study of 119 Patients," The Annals of otology, Rhinology and Laryngology, Mar. 1992, vol. 101 (3), pp. 237-247.

(56) References Cited

OTHER PUBLICATIONS

Frey P., et al., "Subureteral Collagen Injection for the Endoscopic Treatment of Vesicoureteral Reflux in Children. Followup Study of 97 Treated Ureters and Histological Analysis of Collagen Implants," The Journal of Urology, Aug. 1992, vol. 148 (2 Pt 2), pp. 718-723.
Giordano A., et al., "From the Laboratory Bench to the Patient's Bedside: An Update on Clinical Trials with Mesenchymal Stem Cells," Department of Experimental Medicine of Biotechnology and Molecular Biology, Second University of Naples, Oct. 2006, 10 pages.
Greenwood J., et al., "Real-Time Demonstration of Split Skin Graft Inosculation and Integra Dermal Matrix Neovascularization Using Confocal Laser Scanning Microscopy," Journal of Plastic Surgery, Aug. 2009, vol. 9, pp. e33.
Hallock G.G., "The Cosmetic Split-Thickness Skin Graft Donor Site," Plastic and Reconstructive Surgery, 1999, vol. 104 (7), pp. 2286-2288.
Hansbrough W., et al., "Management of Skin-Grafted Burn Wounds with Xeroform and Layers of Dry Coarse-Mesh Gauze Dressing Results in Excellent Graft Take and Minimal Nursing Time," Journal of Burn Care and Rehabilitation, 1995, vol. 16 (5), pp. 531-534.
Hazani R., et al., "Optimizing Aesthetic Results in Skin Grafting," The American Surgeon, Feb. 2012, vol. 78 (2), pp. 151-154.
International Search Report and Written Opinion for Application No. PCT/US2017/017683, dated Jul. 27, 2017, 10 pages.
International Search Report and Written Opinion for Application No. PCT/US2017/030840, dated Oct. 3, 2017, 15 pages.
International Search Report and Written Opinion for Application No. PCT/US2018/017100, dated Sep. 12, 2018, 18 pages.
International Search Report and Written Opinion for Application No. PCT/US2018/32387, dated Jan. 7, 2019, 15 pages.
International Search Report and Written Opinion for Application No. PCT/US2019/037484, dated Jan. 7, 2020, 15 pages.
International Search Report and Written Opinion for Application No. PCT/US2013/073678, dated May 27, 2014, 18 pages.
International Search Report and Written Opinion for Application No. PCT/US2014/058886, dated Mar. 2015, 22 pages.
International Search Report and Written Opinion for Application No. PCT/US2015/047695, dated Jan. 28, 2016, 40 pages.
International Search Report and Written Opinion for Application No. PCT/US2015/047721, dated Feb. 3, 2016, 20 pages.
International Search Report and Written Opinion for Application No. PCT/US2016/016834, dated May 17, 2016, 11 pages.
Ito K., et al., "Biology of Fracture Healing," AO Principles of Fracture Management, AO Foundation Publishing, Jan. 2013, 5 pages.
Jones L.M., "The Biobrane Stent," Journal of Burn Care and Rehabilitation, 1998, vol. 19 (4), pp. 352-353.
Kaplan E.N., et al., "Clinical Utilization of Injectable Collagen," Annals of Plastic Surgery, Jun. 1983, vol. 10 (6), pp. 437-451.
Klein A.W., et al., "Implantation Technics for Injectable Collagen," Journal of the American Academy of Dermatology, Aug. 1983, vol. 9 (2), pp. 224-228.
Kogan L., et al., "Vertical (Two-Layer) Skin Grafting: New Reserves for Autologic Skin," Annals of Plastic Surgery, 2003, vol. 50 (5), pp. 514-516.
Lee H., et al., "Outcomes of Sprayed Cultured Epithelial Autografts for Full-Thickness Wounds: A Single-Centre Experience," Burns, 2012, vol. 38 (6), pp. 931-936.
Lindenblatt N., et al., "A New Model for Studying the Revascularization of Skin Grafts in Vivo: The Role of Angiogenesis," Plastic and Reconstructive Surgery, 2008, vol. 122 (6), pp. 1669-1680.

Matton G., et al., "The History of Injectable Biomaterials and the Biology of Collagen," Aesthetic Plastic Surgery, Jun. 1985, vol. 9 (2), pp. 133-140.
Mimoun M., et al., "The Scalp is an Advantageous Donor Site for Thin-Skin Grafts: A Report on 945 Harvested Samples," Plastic and Reconstructive Surgery, 2006, vol. 118 (2), pp. 369-373.
Mottura A.A., et al., "Open Frontal Lift: A Conservative Approach," Aesthetic Plastic Surgery, 2006, vol. 30 (4), pp. 381-389.
O'Connor K.W., et al., "Endoscopic Placement of Collagen at the Lower Esophageal Sphincter to Inhibit Gastroesophageal Reflux: a Pilot Study of 10 Medically Intractable Patients," Gastrointestinal Endoscopy, 1988, vol. 34 (2), pp. 106-112.
Pallua N., et al., "The Lipo-Facelift: Merging the Face-Lift and Liposculpture: Eight Years Experience and a Preliminary Observational Study," Aesthetic Plastic Surgery, 2013, vol. 37 (6), pp. 1107-1113.
Penington A.J., et al., "Skin Graft Failure Is Predicted by Waist-Hip Ratio: Marker for Metabolic Syndrome," ANZ Journal of Surgery, 2007, vol. 77 (3), pp. 118-120.
Polder K.D., et al., "Radiofrequency: Thermage," Facial Plastic Surgery Clinics of North America, 2011, vol. 19 (2), pp. 347-359.
Russe E et al., "Micro-Fractional, Direction Skin Tightening: A Porcine Model," Lasers in Surgery and Medicine, Mar. 2016, vol. 48 (3), pp. 264-269.
Sheridan R.L., et al., "Initial Experience with a Composite Autologous Skin Substitute," Burns, 2000, vol. 27 (5), pp. 421-424.
Shortliffe L.M., et al., "Treatment of Urinary Incontinence by the Periurethral Implantation of Glutaraldehyde Cross-Linked Collagen," The Journal of Urology, Mar. 1989, vol. 141 (3), pp. 538-541.
Sklar L.R., et al., "Use of Transcutaneous Ultrasound for Lipolysis and Skin Tightening: A Review," Aesthetic Plastic Surgery, 2014, vol. 38 (2), pp. 429-441.
Sukal S.A., et al., "Thermage: The Nonablative Radiofrequency for Rejuvenation," Clinics in Dermatology, 2008, vol. 26 (6), pp. 602-607.
Supplementary European Search Report for Application No. EP14850567 dated May 4, 2017, 4 pages.
Supplementary European Search Report for Application No. EP15836045 dated Jan. 8, 2018, 7 pages.
Supplementary European Search Report for Application No. EP17750972 dated Sep. 13, 2019, 8 pages.
Supplementary European Search Report for Application No. EP17793252 dated Nov. 22, 2019, 7 pages.
Supplementary European Search Report for Application No. EP13859972, dated Jun. 10, 2016, 6 pages.
Thourani V.H., et al., "Factors Affecting Success of Split-Thickness Skin Grafts in the Modern Burn Unit," The Journal of Trauma, Mar. 2003, vol. 54 (3), pp. 562-568.
Wells M.D., et al., "A New Method of Skin-Graft Stabilization: The Reston Technique," Annals of Plastic Surgery, 1995, vol. 34 (5), pp. 554-556.
Wendt J.R., et al., "Long-Term Survival of Human Skin Allografts in Patients with Immunosuppression," Plastic and Reconstructive Surgery, Apr. 2004, vol. 133 (5), pp. 1347-1354.
Williamson J. S., et al., "Cultured Epithelial Autograft: Five Years of Clinical Experience with Twenty-Eight Patients," The Journal of Trauma, Aug. 1995, vol. 39 (2), pp. 309-319.
Wood F.M., et al., "The Use of Cultured Epithelial Autograft in the Treatment of Major Burn Injuries: A Critical Review of the Literature," Burns, 2006, vol. 32 (4), pp. 395-401.
Zuber T.J., "Fusiform Exision," American Family Physician, Apr. 2003, vol. 67 (7), pp. 1539-1544.

* cited by examiner

SKIN TREATMENT DEVICE

RELATED APPLICATIONS

This application is a continuation of U.S. patent application Ser. No. 14/556,648, filed Dec. 1, 2014, now U.S. Pat. No. 9,987,473, which is a continuation of U.S. patent application Ser. No. 12/972,013, filed Dec. 17, 2010, now U.S. Pat. No. 8,900,181, which claims priority to U.S. Provisional Patent Application No. 61/288,141, filed Dec. 18, 2009, all of which are hereby incorporated herein by reference.

BACKGROUND

The aging process is most visibly depicted by the development of dependent skin laxity. This life long process may become evident as early as the third decade of life and will progressively worsen over subsequent decades. Histological research has shown that dependant stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas is the head and neck. In this region, prominent "turkey gobbler" laxity of neck and "jowls" of the lower face are due to an unaesthetic dependency of skin in these areas. The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Some of the inherent adverse features of these surgical procedures are post-operative pain, scarring and the risk of surgical complications. Even though the aesthetic enhancement of these procedures is an acceptable tradeoff to the significant surgical incisions required, permanent and extensive scarring is always an incumbent part of these procedures. For this reason, Plastic Surgeons design these procedures to hide the extensive scarring around anatomical borders such as the hairline (Facelift), the inframmary fold (Mastopexy) and the inguinal crease (Abdominoplasty). However, other skin laxity regions such as the Suprapatellar (upper-front) knee are not amendable to Plastic Surgical resections due to the poor tradeoff with a more visible surgical scar. Recently, electromagnetic medical devices that create a reverse thermal gradient (i.e., Thermage) have attempted with variable success to tighten skin without surgery. At this time, these electromagnetic devices are best deployed in patients with a moderate amount of skin laxity due to the limitations of electromagnetic devices and potential side effects of surgery.

The foregoing examples of the related art and limitations related therewith are intended to be illustrative and not exclusive. Other limitations of the related art will become apparent upon a reading of the specification and a study of the drawings.

DETAILED DESCRIPTION OF EMBODIMENTS

Figure 1A:
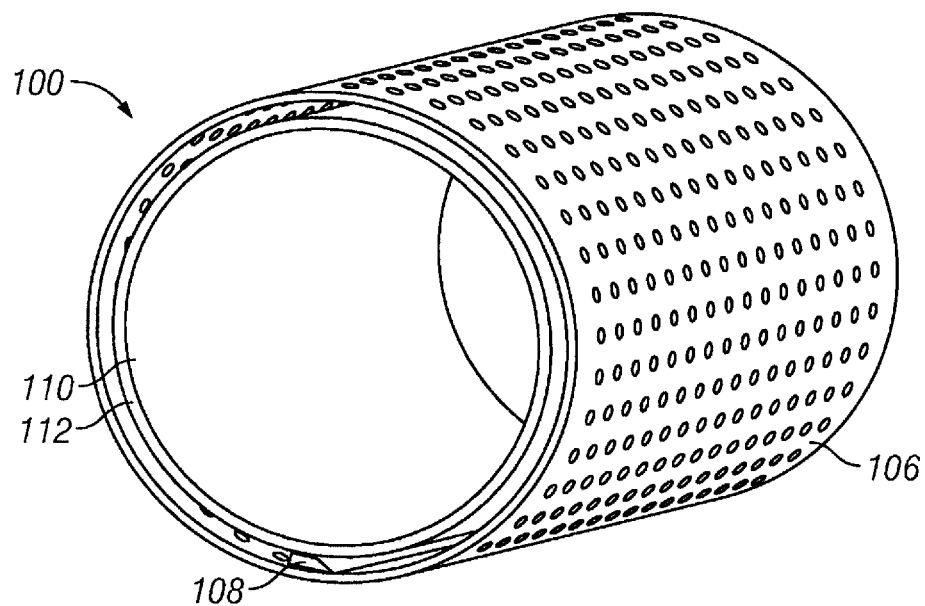
FIGS. 1(a)-(c) depict examples of a full rolling/rotating pixel drum/cylinder applicable to a skin surface for tightening.

The approach is illustrated by way of example and not by way of limitation in the figures of the accompanying drawings in which like references indicate similar elements. It should be noted that references to "an" or "one" or "some" embodiment(s) in this disclosure are not necessarily to the same embodiment, and such references mean at least one.

A new minimally invasive surgical approach is proposed that contemplates a method and apparatus for tightening lax skin without visible scarring via a device in various surgical procedures such as plastic surgery procedures. In some embodiments, the device is a single use disposable instrument. This approach circumvents surgically related scarring and the clinical variability of electromagnetic heating of the skin and performs small multiple pixilated resections of skin as a minimally invasive alternative to large Plastic surgical resections of skin. This approach can also be employed in areas of the body that are currently off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast), the minimally invasive surgical approach performs pixilated transection/resection of excess skin, replacing Plastic Surgery with its incumbent scarring. Typically, the procedure will be performed in an office setting under a local anesthetic with minimal perioperative discomfort. In comparison to a prolonged healing phase from plastic surgery, only a short recovery period will be required and the only recovery requirement will be the need to wear a support garment over the treatment area for 5 days. There will be little or no pain associated with the procedure. The small (½ mm to1mm) intradermal circular skin defects will be closed with the application of an adherent Flexan (3M) sheet. Functioning as a large butterfly bandage, the Flexan sheet can be pulled in a direction ("vector") that maximizes the aesthetic contouring of the treatment area. A compressive elastic garment will be applied over the dressing to further assist aesthetic contouring. After completion of the initial healing phase, the multiplicity of small linear scars within the treatment area will not be visibly apparent. It is also predicted that additional skin tightening will occur subsequently over several months due to the delayed wound healing response. Other potential applications include the treatment of Snoring/Sleep apnea, Orthopedics/Physiatry, Vaginal Tightening and tightening of gastrointestinal sphincters. During recovery, the treatment area is covered with a Flexan dressing and a compressive garment that promotes the wound healing process in the most effective direction.

Device for Skin Treatment

Figure 1B:
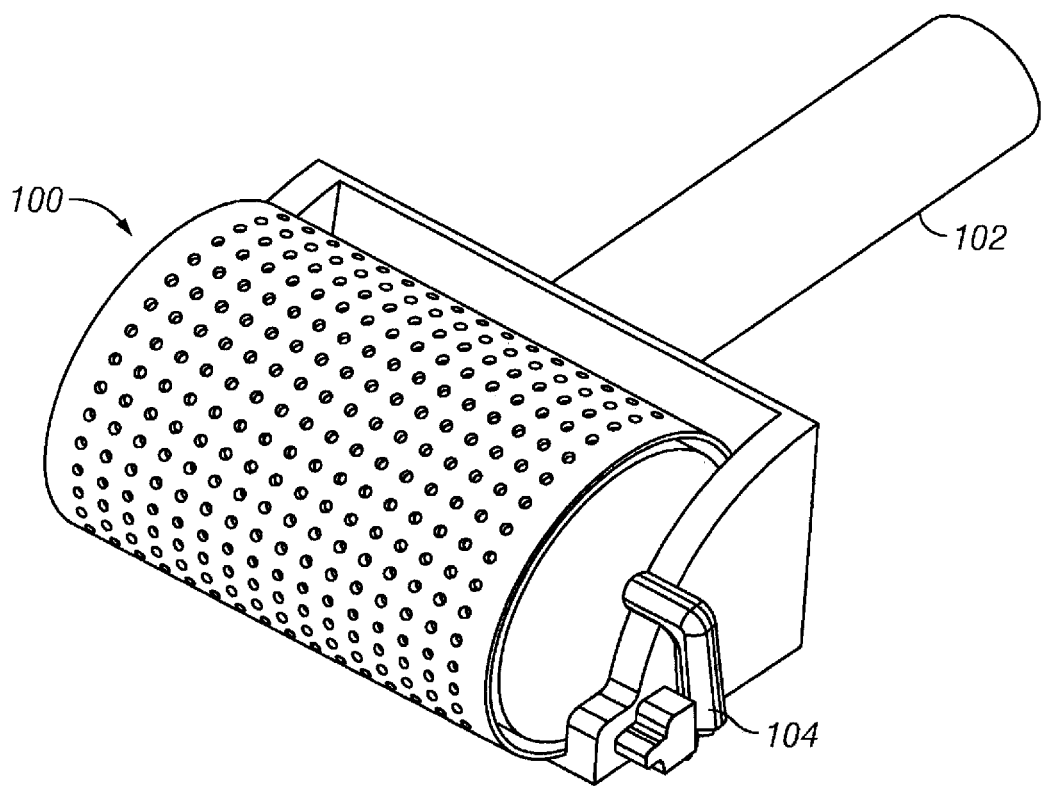
Figure 1C:
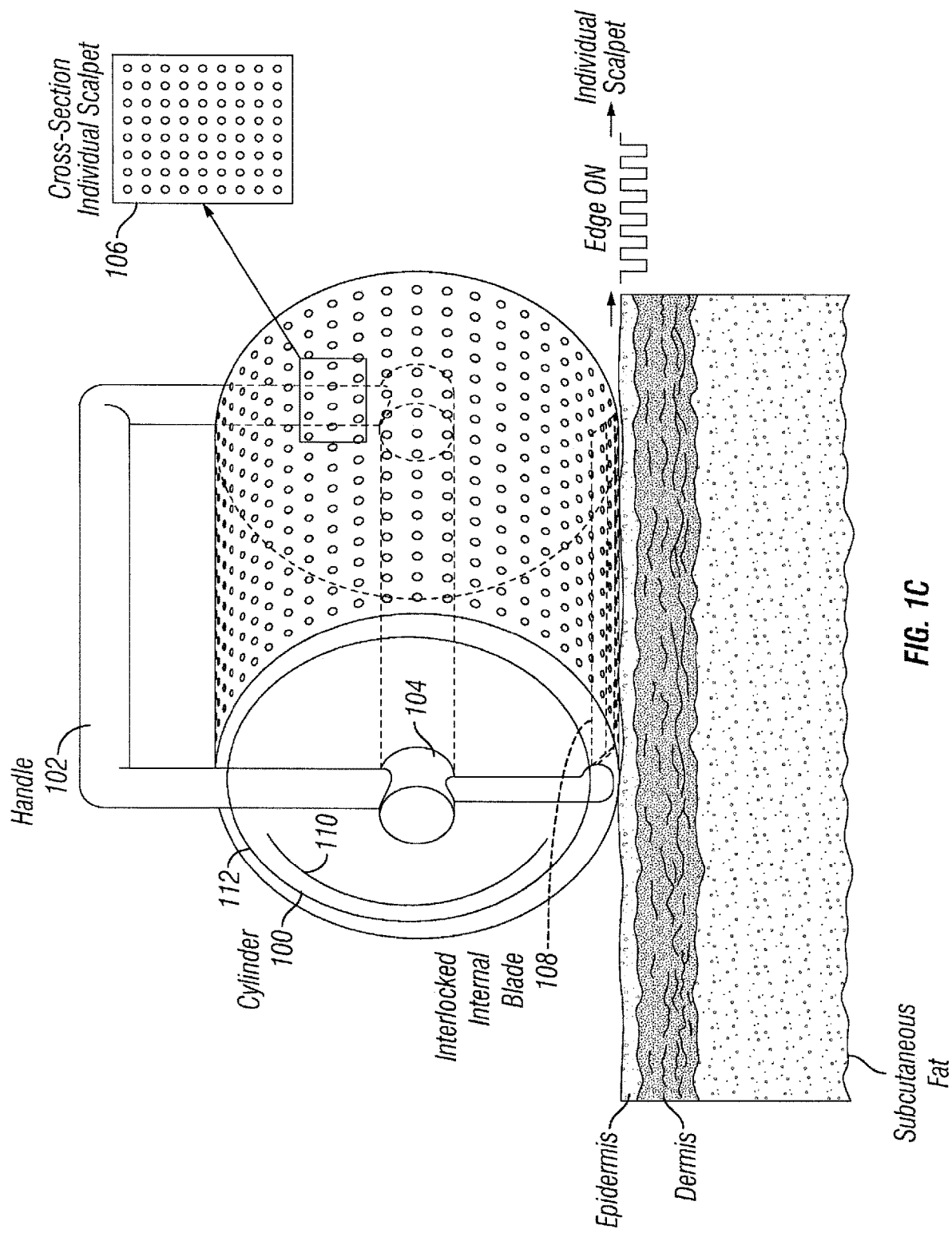

FIGS. 1(a)-(c) depict examples of a full rolling/rotating pixel drum/cylinder 100 applicable to the skin surface for tightening. Although the diagrams depict components as functionally separate, such depiction is merely for illustrative purposes. It will be apparent that the components portrayed in this figure can be arbitrarily combined or divided into separate hardware components.

Referring now to FIGS. 1(a)-(c), FIG. 1(a) depicts an example of rolling pixel drum 100, FIG. 1(b) depicts an example of a rolling pixel drum 100 assembled on a handle, and FIG. 1(c) depicts an example of a rolling pixel drum 100 being applied to the skin surface for tightening. FIGS. 2(a)-(d) further depict examples of dissected internal structure of a half drum depicted in FIGS. 1(a)-(d).

As with other pixel devices, the geometry of the pixel drum 100 can be a variety of shapes without limitation i.e., circular, semicircular, elliptical, square, flat, or rectangular. In some embodiments, the pixel drum 100 is supported by an axel/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., ½ mm to 1 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axel/handle assembly 102 and/or connected to outriggers attached to the central axel assembly 102. In some alternative embodiments, the internal blade 108 is not connected to the drum axel assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin can be transected. It is predicted that up to 50% of the skin's surface area can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In some embodiments, the blade 108 is placed external to the drum 100 and the scalpet array 106 where the base of the incised circular skin plugs is transected. In some embodiments, the external blade 108 is connected to the drum axel assembly 102 when the base of the incisions of skin is transected. In some alternative embodiments, the external blade 108 is not connected to the drum axel assembly 102 when the base of the incisions of skin is transected. The adherent membrane 110 that extracts and aligns the transected skin segments onto the membrane 110, which is later placed over a skin defect site of a patient. In some embodiments, blade 108 (either internal or external) can be a fenestrated layer of blade aligned to the scalpet array 106.

Figure 2A:
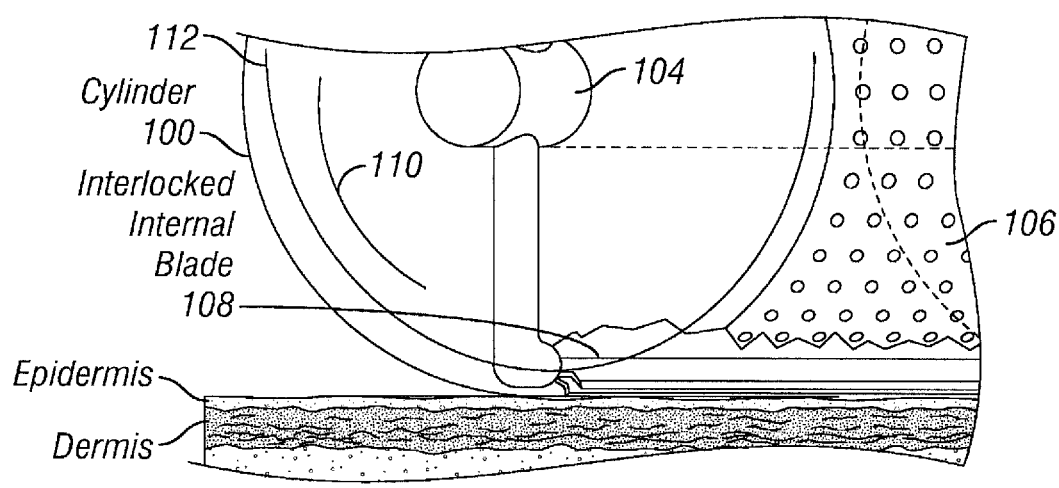
FIGS. 2(a)-(d) depict examples of dissected internal structure of a half drum depicted in FIGS. 1(a)-(d).
Figure 2B:
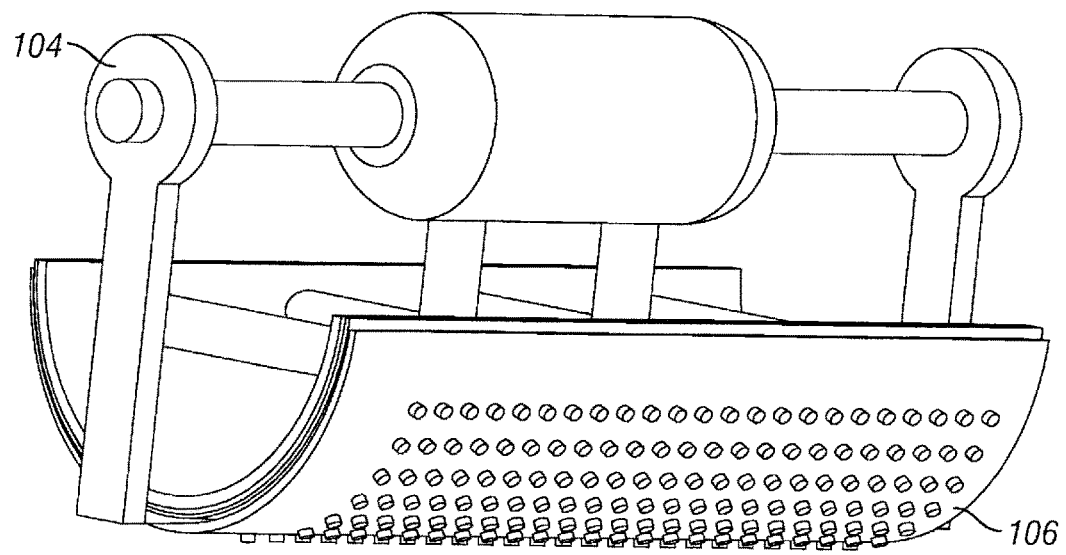
Figure 2C:
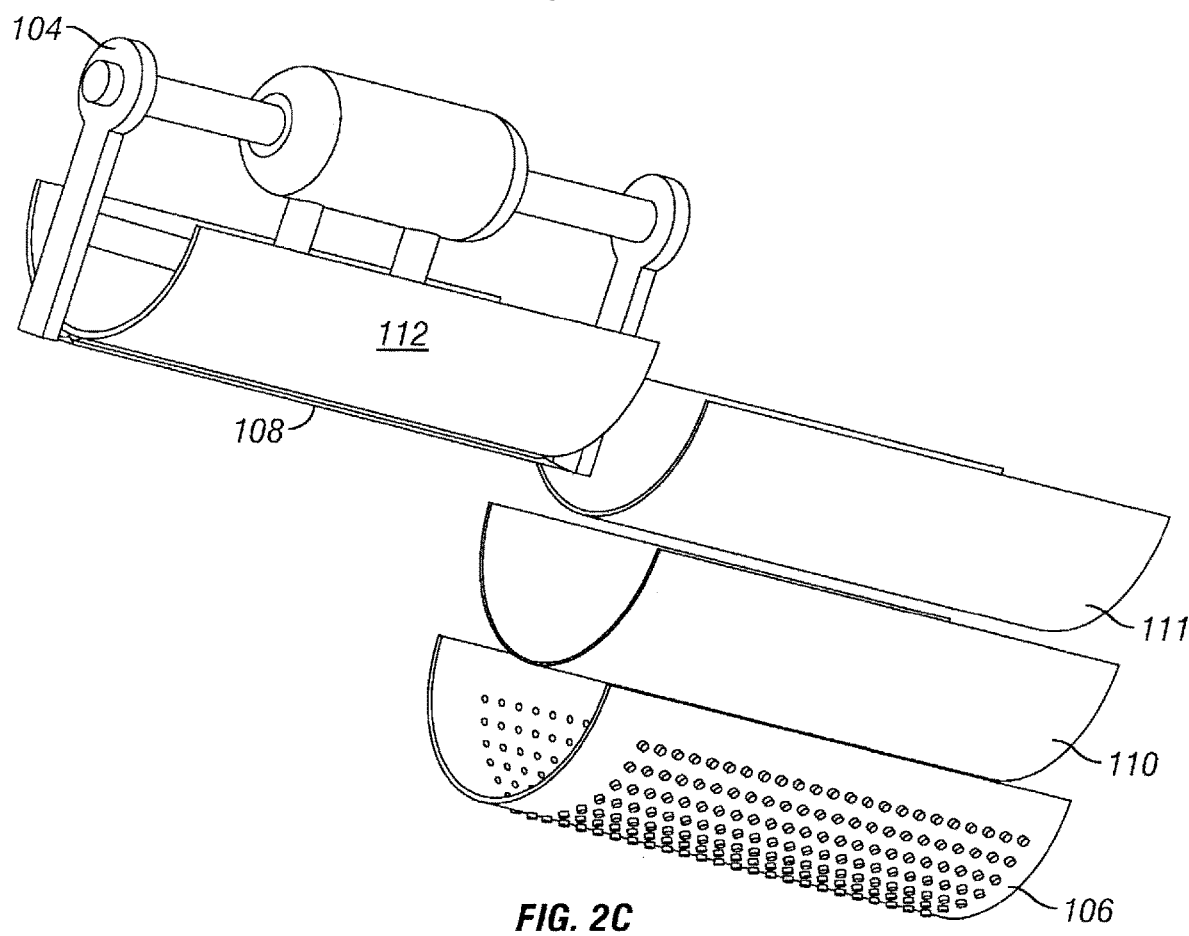
Figure 2D:
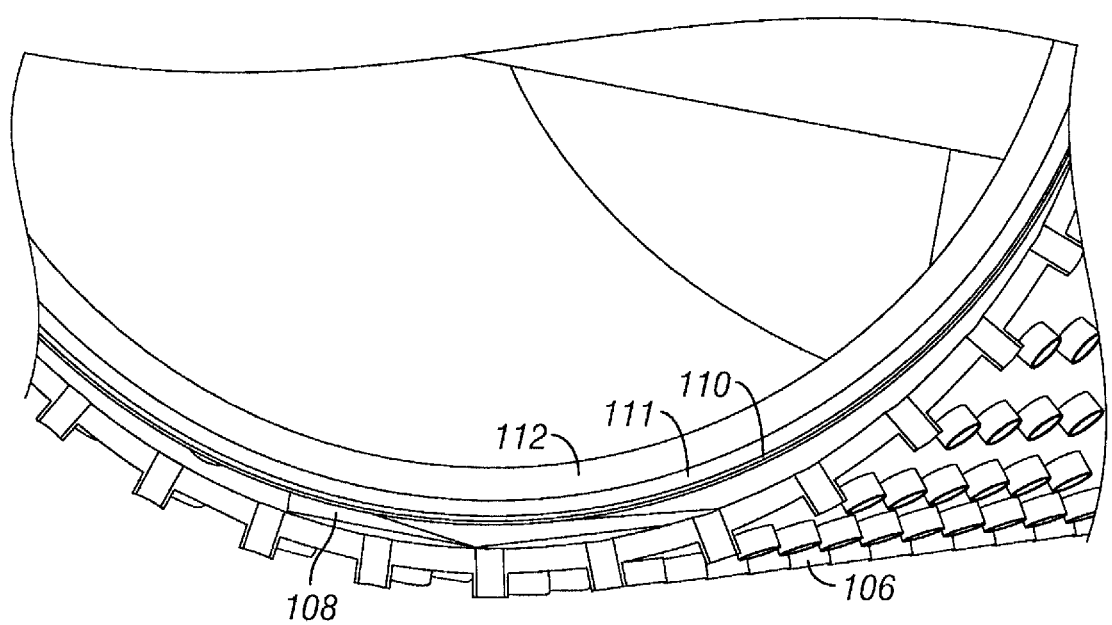

In some embodiments, the conformable adherent membrane 110 can be semi-porous to allow for drainage at a recipient skin defect when the membrane with the aligned transected skin segments is extracted from the drum and applied as a skin graft. In some embodiments, the adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. In some embodiments, the adherent semi-porous drum membrane 110 can also be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100 as shown in FIGS. 2(c)-(d).

In some embodiments, the internal drum harvester 112 of the pixel drum 110 is disposable and replaceable. Limit and/or control the use of the disposable components can be accomplished by means that includes but is not limited to electronic, eprom, mechanical, durability. The electronic and/or mechanical records and/or limits of number of drum rotations for the disposable drum as well as the time of use for the disposable drum can be recorded, controlled and/or limited either electronically or mechanically.

Figure 3A:
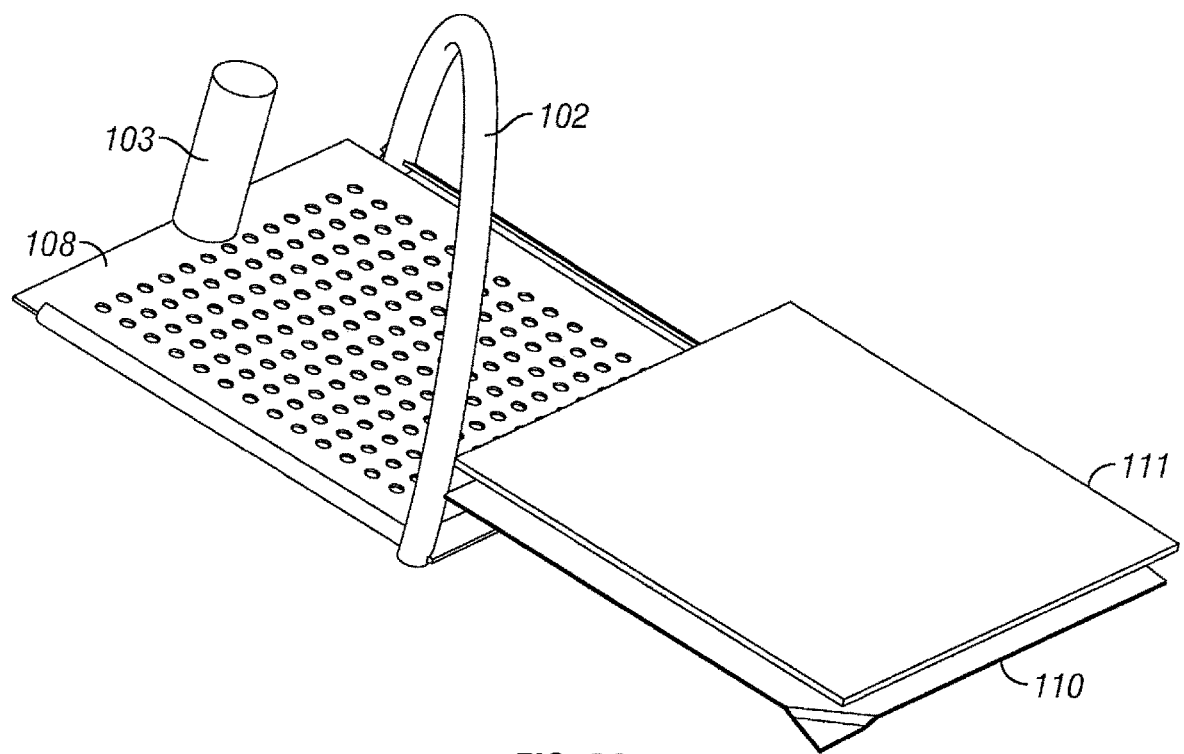
FIGS. 3(a)-(d) depict examples of an oscillating flat array of scalpets and blade either powered electrically or deployed manually (unpowered).
Figure 3B:
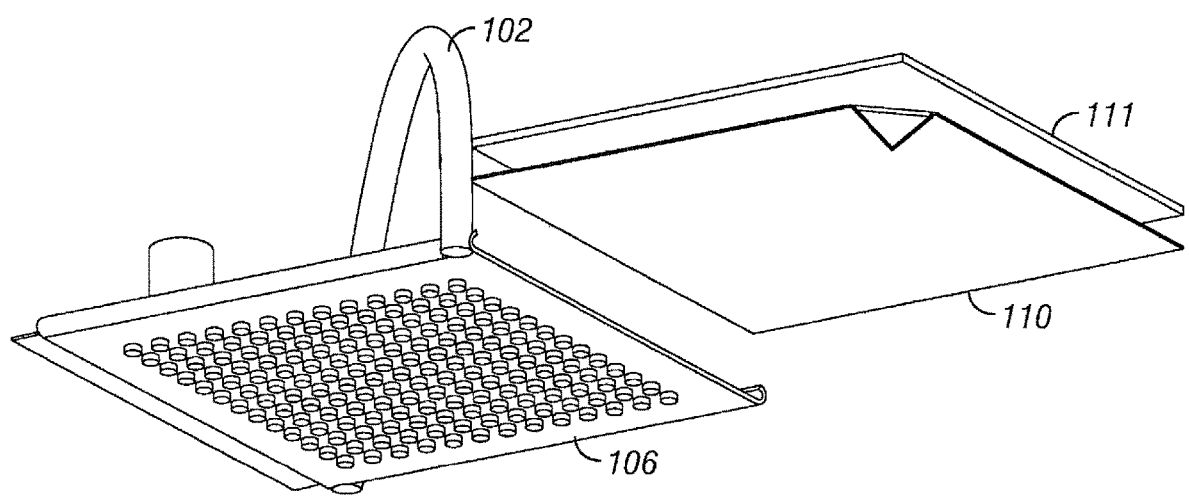
Figure 3C:
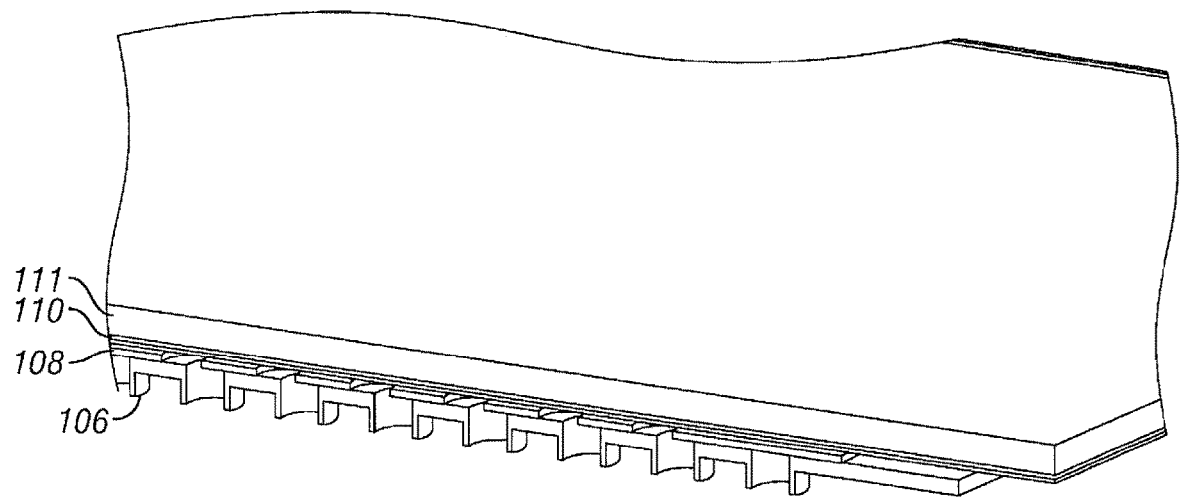
Figure 3D:
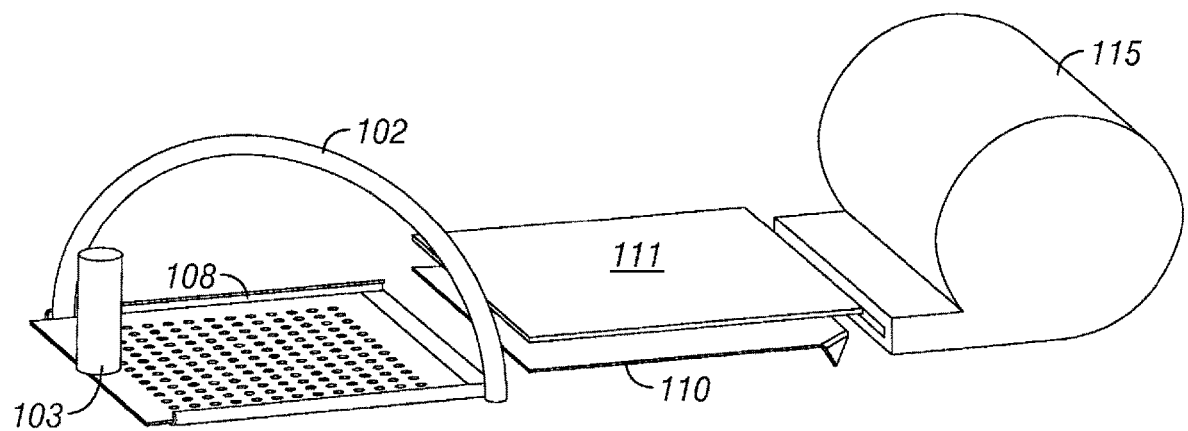

In some embodiments, an oscillating flat array of scalpets and blade as shown in FIGS. 3(a)-(d) either powered electrically or deployed manually (unpowered) can be used for skin tightening as alternative to the drum/cylinder depicted in FIGS. 1(a)-(c) and 2(a)-(d). Here, blade 108 can be a fenestrated layer of blade aligned to the scalpet array 106. FIGS. 3(a)-(b) depict top and bottom views of the flat array where the instrument handle 102 is separated from the blade handle 103 and the adherent membrane 110 can be peeled away from the adhesive backer 111. FIG. 3(c) depict a close-up view of the flat array when the array of scalpets 106, blades 108, adherent membrane 110 and the adhesive backer 111 are assembled together. As assembled, the flat array of scalpets can be metered to provide a uniform harvest or a uniform resection. In some embodiments, the flat array of scalpets may further include a feeder component 115 for the adherent harvesting membrane 110 and adhesive backer 111 as shown in FIG. 3(d).

Figure 4:
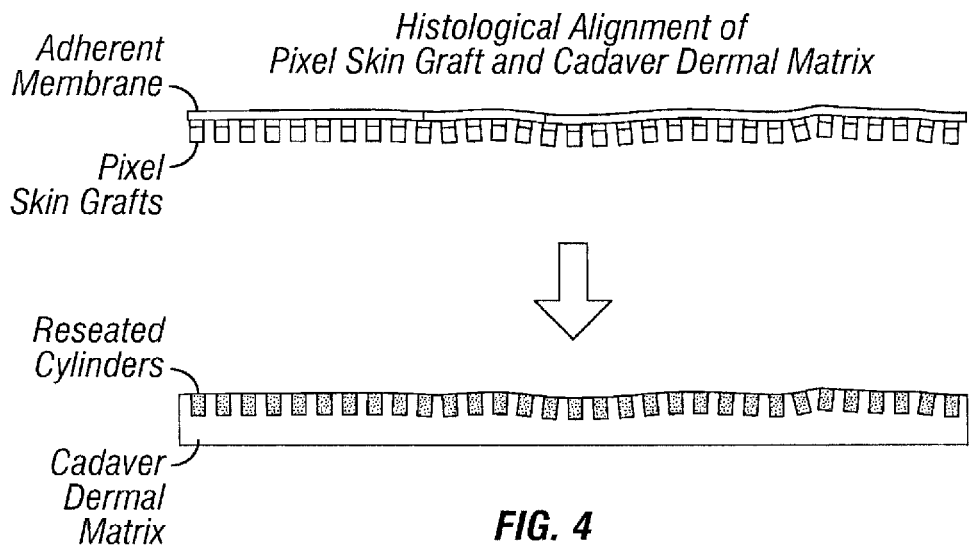
FIG. 4 depicts an example of a cadaver dermal matrix cylindrical transected similar in size to the harvested skin pixel grafts to provide histological alignment of the pixilated graft into the cadaver dermal framework.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In some embodiments, the cadaver dermal matrix can also be cylindrical transected similar in size to the harvested skin pixel grafts to provide histological alignment of the pixilated graft into the cadaver dermal framework as shown in FIG. 4. In some embodiments, the percentage of harvest of the donor site can be determined in part by the induction of a normal dermal histology at the skin defect site of the recipient as shown in FIG. 4, i.e., a normal (smoother) surface topology of the skin graft is facilitated. With either the adherent membrane or the dermal matrix embodiment, major advantage of the pixel drum harvester includes the ability to harvest a large surface area for grafting with visible scarring of the patient's donor site significantly reduced or eliminated.

In some embodiments, the pixel drum 100 may evoke cellular and/or extracellular responses that are obligatory to the clinical outcomes achieved and a physical reduction of the skin surface area may occur due to the transected/pixilated skin, i.e., creation of the skin plugs. In addition, a subsequent tightening of the skin is predicted due to the delayed wound healing response. Each skin pixilation may initiate the obligate wound healing sequence in multiple phases:

The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.

The second phase (of Fibroplasia) commences within 4-5 days of "wounding". During this phase, there is migration and mitotic multiplication of fibroblasts. Fibroplasia of the wound has two key features: the deposition of neocollagen and the myofibroblastic contraction of the wound. Histologically, the deposition of neocollagen can be identified microscopically as compaction and thickening of the dermis. Although this is a static process, the tensile strength of the wound significantly increases. The other feature of Fibroplasia is a dynamic physical process that results in a three dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia will be dermal contraction along with the deposition of a static supporting scaffolding of neocollagen with a tightened framework. The clinical effect can be seen as a delayed tightening of skin with smoothing of skin texture over several months. The clinical endpoint is a more youthful appearing skin envelope of the treatment area.

A third and final phase of the delayed wound healing response is maturation. During this phase there is a strengthening and remodeling of the treatment area due to an increased cross-linkage of the collagen fibril matrix (of the dermis). This final stage commences with 6 to 12 months after "wounding" and may extend for at least 1-2 years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel drum 100 described above may have additional medically related applications. In some embodiments, the pixel drum 100 can transect a variable portion of any soft tissue structure without resorting to a standard surgical resection. More specifically, the reduction of an actinic damaged area of skin via the pixel drum 100 should reduce the incidence of skin cancer. For the treatment of sleep apnea and snoring, a pixilated mucosal reduction (soft palate, base of the tongue and lateral pharyngeal walls) via the pixel drum 100 would reduce the significant morbidity associated with more standard surgical procedures. For birth injuries of the vaginal vault, pixilated skin and vaginal mucosal resection via the pixel drum 100 would reestablish normal pre-partum geometry and function without resorting to an A&P resection. Related female stress incontinence could also be corrected in a similar fashion.

Drug Delivery Device

For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 5:
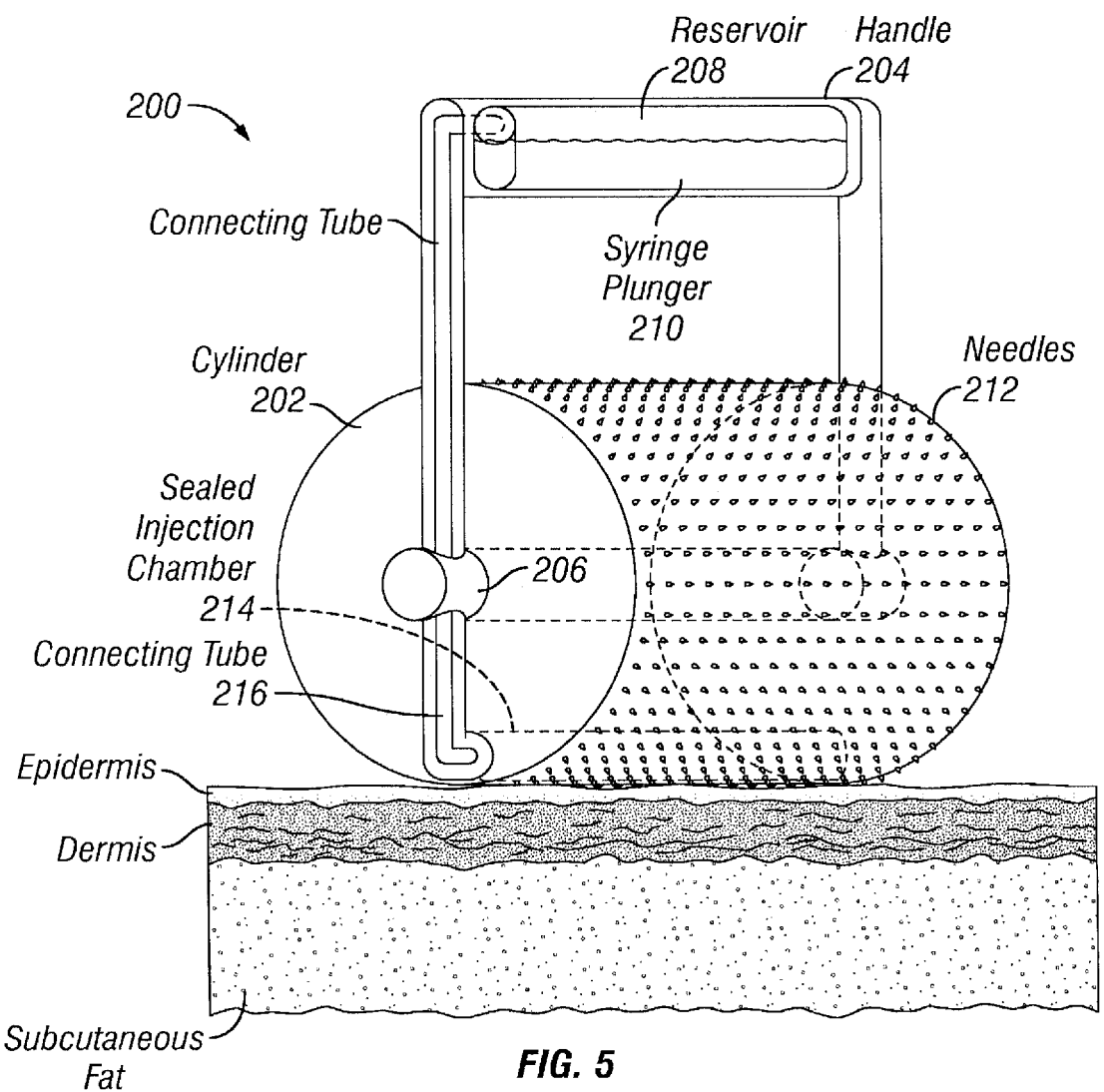
FIG. 5 depicts example of a drum-based drug delivery device being applied to the skin surface for drug injection.

The drug delivery device 200 depicted in FIG. 5 successfully addresses the limitations and drawbacks of other drug delivery systems. A drum/cylinder 202 depicted in FIG. 5 is supported by an axel/handle assembly 204 and rotated around a drum rotation component 206. The handle assembly 204 may further include a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 6A:
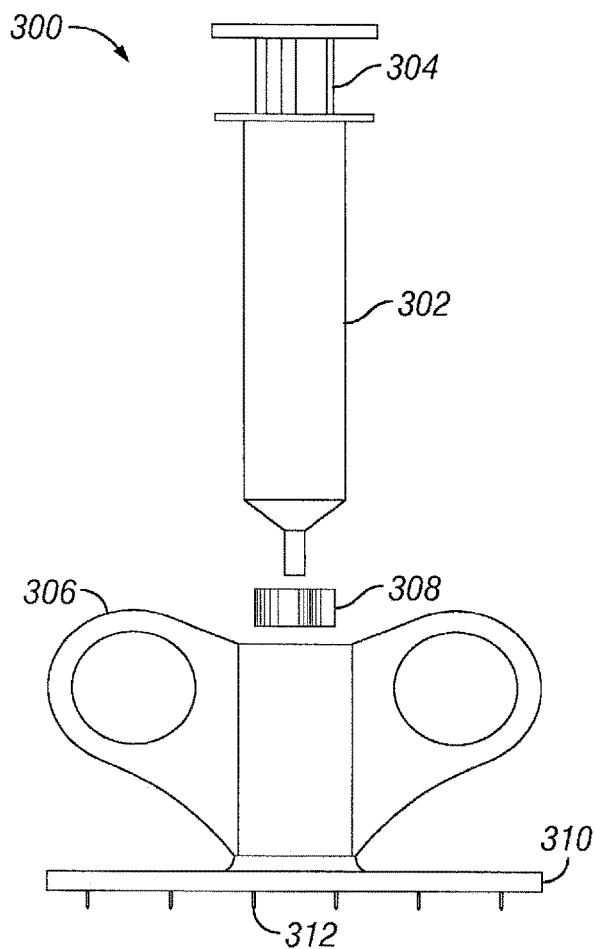
FIG. 6(a)-(c) depict examples of a drug delivery device based on flat array of needles being applied to the skin surface for drug injection.
Figure 6B:
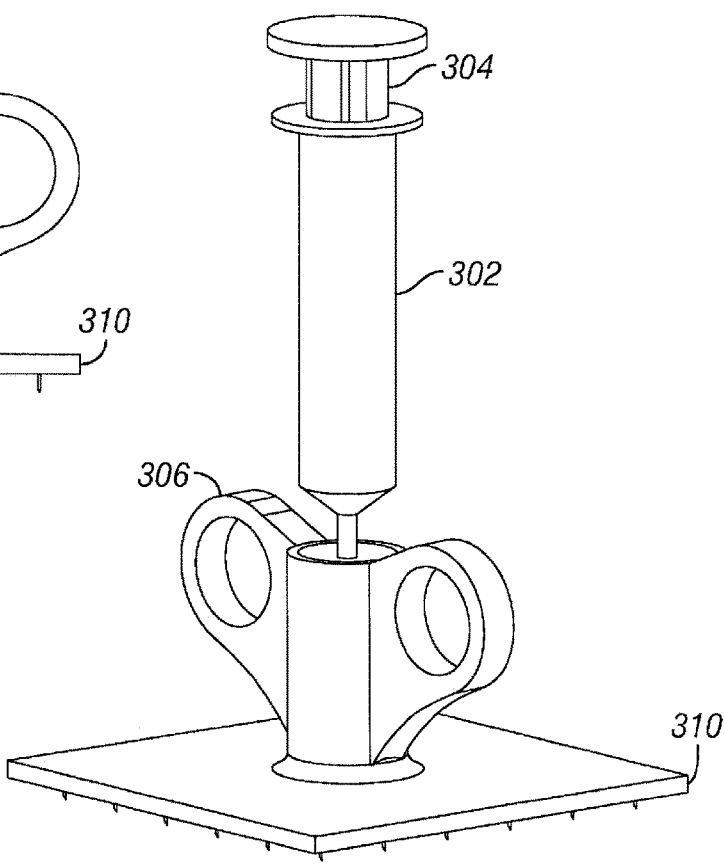
Figure 6C:
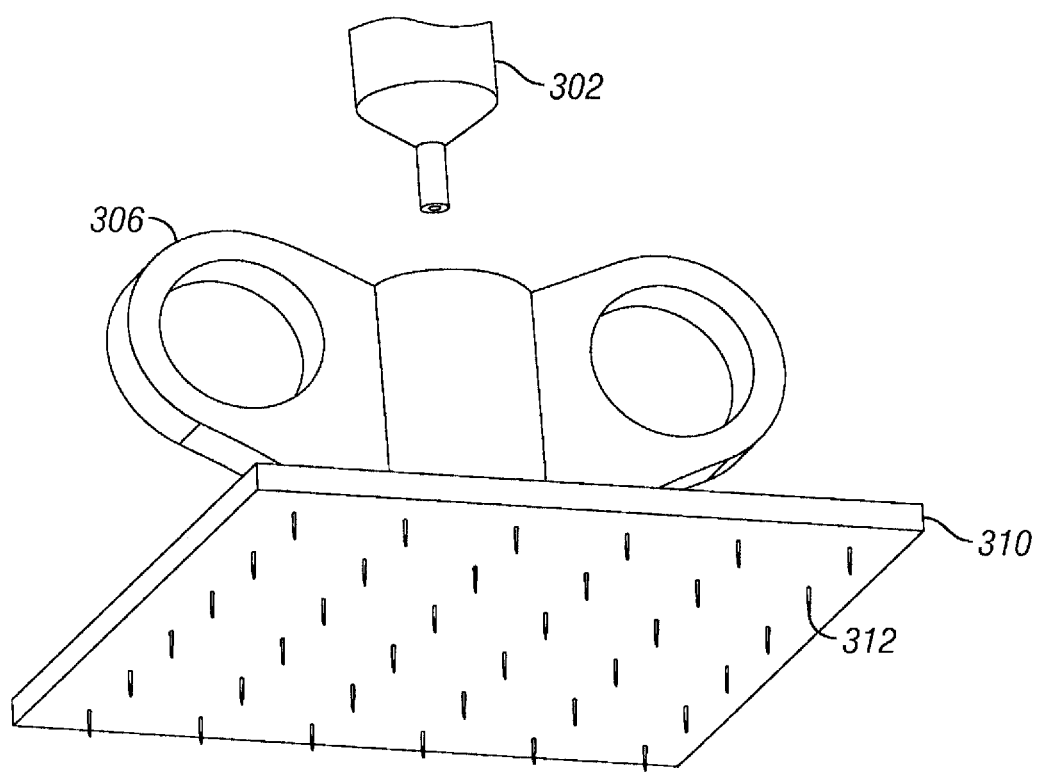

FIGS. 6(a)-(c) depict alternative embodiments of a drug delivery device 300, where a flat array of fine needles 312 of uniform length positioned on manifold 310 can be utilized for drug delivery. In the examples of FIG. 6(a), syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin. FIGS. 6(b)-(c) depict top and bottom views of the drug delivery device 300 with a flat array of fine needles 312, respectively.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

The foregoing description of various embodiments of the invention has been presented for purposes of illustration and description. Various methods of the invention are applicable to variety of medical, dermatological and surgical methods including reconstructive and plastic surgery procedures and minimally invasive procedures. It is not intended to limit the invention to the precise forms disclosed. Many modifications, variations and different combinations of embodiments will be apparent to practitioners skilled in this art. Further, elements from one embodiment can be readily recombined with one or more elements from other embodiments.

What is claimed is:

1. A system, comprising:
   a scalpet assembly comprising a scalpet array, wherein the scalpet array includes scalpets, wherein each scalpet comprises a cylindrical scalpet with a circular cross-section and a distal end configured to generate circular incisions including a diameter approximately in a range of 0.5 millimeters (mm) to 2.0 mm, wherein the scalpet array is configured to be deployed to a plurality of target sites to generate a plurality of incised skin pixels at the plurality of target sites; and
   a capture system configured to capture the plurality of incised skin pixels at the plurality of target sites.

2. The system of claim 1, wherein the distal end of the scalpets includes a sharpened edge.

3. The system of claim 1, wherein an interior region of the scalpets includes a hollow region.

4. The system of claim 1, wherein the generation of the plurality of incised skin pixels includes generation of a plurality of skin defects configured to evoke neovascularization at the plurality of target sites.

5. The system of claim 1, wherein the generation of the plurality of incised skin pixels includes generation of a plurality of skin defects configured to evoke a wound healing response at a recipient site.

6. The system of claim 1, wherein the plurality of target sites includes at least one of a donor site and a recipient site.

7. The system of claim 6, wherein the plurality of incised skin pixels is harvested at the donor site.

8. The system of claim 7, wherein the generation of the plurality of incised skin pixels includes generation of a plurality of skin defects at the recipient site, wherein the plurality of skin defects is configured to receive a skin graft comprising the plurality of incised skin pixels from the plurality of target sites.

9. The system of claim 8, wherein the capture system includes an adherent substrate configured to at least one of capture the plurality of incised skin pixels at the donor site and transfer the plurality of incised skin pixels to the recipient site.

10. The system of claim 9, wherein the adherent substrate is configured to maintain relative positioning of the plurality of incised skin pixels during transfer to and application at the recipient site.

11. The system of claim 9, wherein the adherent substrate is configured to apply the plurality of incised skin pixels to the skin defects at the recipient site.

12. The system of claim 9, wherein the adherent substrate is configured to align the plurality of incised skin pixels with the skin defects at the recipient site.

13. The system of claim 9, wherein the adherent substrate is configured as a bandage and to apply force to close the plurality of target sites, wherein the force includes a directional force configured to control a direction of the closure at the plurality of target sites.

14. The system of claim 1, wherein the capture system includes an adherent substrate configured to capture the plurality of incised skin pixels.

15. The system of claim 14, wherein the adherent substrate comprises at least one of a flexible substrate and a semi-porous membrane.

16. The system of claim 1, wherein the capture system includes a vacuum system configured to evacuate tissue including the plurality of incised skin pixels from the plurality of target sites.

17. The system of claim 1, wherein the capture system is coupled to the scalpet assembly.

18. The system of claim 1, comprising at least one bandage configured for application at the plurality of target sites, wherein the at least one bandage is configured to apply force to close the plurality of target sites, wherein the force includes a directional force configured to control a direction of the closure at the plurality of target sites.

19. The system of claim 1, comprising a powered component coupled to the scalpet assembly.

20. The system of claim 19, wherein the powered component includes a rotational component configured to couple a rotational force to the scalpets.

21. The system of claim 1, comprising a cutting member configured to transect the plurality of incised skin pixels.

* * * * *